United States Patent
Frank et al.

(10) Patent No.: US 9,993,004 B2
(45) Date of Patent: *Jun. 12, 2018

(54) METHOD FOR INCREASING THE VIGOR AND/OR CROP YIELD OF AGRICULTURAL PLANTS UNDER ESSENTIALLY NON-EXISTENT PATHOGEN PRESSURE

(71) Applicant: Bayer CropScience LP, Research Triangle Park, NC (US)

(72) Inventors: Markus Frank, Neustadt (DE); David Ernest Silva, Nipomo, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/662,179

(22) Filed: Mar. 18, 2015

(65) Prior Publication Data

US 2015/0208666 A1 Jul. 30, 2015

Related U.S. Application Data

(63) Continuation of application No. 13/318,613, filed as application No. PCT/EP2010/055947 on May 3, 2010, now abandoned.

(60) Provisional application No. 61/175,818, filed on May 6, 2009, provisional application No. 61/176,511, filed on May 8, 2009.

(51) Int. Cl.
*A01N 63/00* (2006.01)
*A01N 43/653* (2006.01)
*A01N 63/04* (2006.01)
*A01N 47/30* (2006.01)
*A01N 55/02* (2006.01)
*A01N 59/20* (2006.01)

(52) U.S. Cl.
CPC ........... *A01N 63/00* (2013.01); *A01N 43/653* (2013.01); *A01N 47/30* (2013.01); *A01N 55/02* (2013.01); *A01N 59/20* (2013.01); *A01N 63/04* (2013.01); *Y02A 50/356* (2018.01)

(58) Field of Classification Search
CPC ...... A01N 63/00; A01N 43/653; A01N 47/24; A01N 37/46; A01N 57/12; A01N 47/12

USPC .......................................................... 504/117
See application file for complete search history.

(56) References Cited

U.S. PATENT DOCUMENTS

| | | | | |
|---|---|---|---|---|
| 6,060,051 A | * | 5/2000 | Heins | A01N 63/00 424/115 |
| 2008/0020999 A1 | * | 1/2008 | Klapproth | A01N 37/52 514/63 |
| 2008/0194585 A1 | | 8/2008 | Sharpe et al. | |

FOREIGN PATENT DOCUMENTS

| | | |
|---|---|---|
| JP | 2003-089612 A | 3/2003 |
| WO | 00/29426 A1 | 5/2000 |

OTHER PUBLICATIONS

Gupta, V.K., "Factors Affecting the Production of Antifungal Compounds by Enterobacter aerogenes and Bacillus subtilis, Antagonists of Phytophthora cactorum," J. Phytopathology, 117, 9-16 (1986).

Gupta, V.K., et al., "Factors Affecting the Production of Antifungal Compounds by Enterobacter aerogenes and Bacillus subtilis, Antagonists of Phytophthora cactorum," J. Phytopathology, 1986, vol. 117, pp. 9-16.

* cited by examiner

*Primary Examiner* — Johann R Richter
*Assistant Examiner* — Danielle Sullivan
(74) *Attorney, Agent, or Firm* — Adam L. Lunceford; Michelle L. Samonek

(57) ABSTRACT

A method for increasing the vigor and/or crop yield of agricultural plants under essentially non-existent pathogen pressure, wherein the plants, the plant propagules, the seed of the plants and/or the locus where the plants are growing or are intended to grow are treated with an effective amount of a composition comprising a) the *Bacillus subtilis* strain with NRRL Accession No. B-21661 or a cell-free extract thereof, and/or a mutant of this strain or extract having all the identifying characteristics of the respective strain or extract as component (I), and b) optionally at least one chemical compound as component (II), selected from the active compound groups A) to J): A) strobilurins; B) carboxamides; C) azoles; D) heterocyclic compounds; E) carbamates; F) other active substances; G) growth regulators; H) herbicides; J) insecticides.

16 Claims, No Drawings

METHOD FOR INCREASING THE VIGOR AND/OR CROP YIELD OF AGRICULTURAL PLANTS UNDER ESSENTIALLY NON-EXISTENT PATHOGEN PRESSURE

CROSS-REFERENCE TO RELATED APPLICATION(S)

The present application claims priority to and is a continuation of U.S. patent application Ser. No. 13/318,613, which claims priority as a 35 U.S.C. § 371 National Stage Entry of International Patent Application No. PCT/EP2010/055947, filed May 3, 2010, which in turn claims priority to U.S. Patent Application No. 61/176,511, filed May 8, 2009, and U.S. Patent Application No. 61/175,818, filed May 6, 2009. Each of the foregoing applications is hereby incorporated by reference in its entirety.

The present invention relates to a method for increasing the vigor and/or crop yield of agricultural plants under essentially non-existent pathogen pressure, wherein the plants, the plant propagules, the seed of the plants and/or the locus where the plants are growing or are intended to grow are treated with an effective amount of a composition comprising
  a) the *Bacillus subtilis* strain with NRRL Accession No. B-21661 or a cell-free extract thereof, and/or a mutant of this strain or extract having all the identifying characteristics of the respective strain or extract as component (I), and
  b) optionally at least one chemical compound as component (II), selected from the active compound groups A) to J):
    A) strobilurins selected from the group consisting of azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl(2-chloro-5-[1-(3-methylbenzyloxyimino)-ethyl]benzyl)carbamate and 2-(2-(3-(2,6-dichlorophenyl)-1-methyl-allylideneaminooxymethyl)-phenyl)-2-methoxyimino-N-methyl-acetamide;
    B) carboxamides selected from the group consisting of
      carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;
      carboxylic morpholides: dimethomorph, flumorph, pyrimorph;
      benzoic acid amides: flumetover, fluopicolide, fluopyram, zoxamide, N-(3-Ethyl-3,5,5-trimethyl-cyclohexyl)-3-formylamino-2-hydroxy-benzamide;
      other carboxamides: carpropamid, dicyclomet, mandiproamid, oxytetracyclin, silthiofarm and N-(6-methoxy-pyridin-3-yl)cyclopropanecarboxylic acid amide;
    C) azoles selected from the group consisting of
      triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;
      imidazoles: cyazofamid, imazalil, pefurazoate, prochloraz, triflumizol;
      benzimidazoles: benomyl, carbendazim, fuberidazole, thiabendazole;
      others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;
    D) heterocyclic compounds selected from the group consisting of
      pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide;
      pyrimidines: bupirimate, cyprodinil, diflumetorim, fenarimol, ferimzone, mepanipyrim, nitrapyrin, nuarimol, pyrimethanil;
      piperazines: triforine;
      pyrroles: fenpiclonil, fludioxonil;
      morpholines: aldimorph, dodemorph, dodemorph-acetate, fenpropimorph, tridemorph;
      piperidines: fenpropidin;
      dicarboximides: fluoroimid, iprodione, procymidone, vinclozolin;
      non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;
      others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methyl-piperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E) carbamates selected from the group consisting of
thio- and dithiocarbamates: ferbam, mancozeb, maneb, metam, methasulphocarb, metiram, propineb, thiram, zineb, ziram;
carbamates: benthiavalicarb, diethofencarb, iprovalicarb, propamocarb, propamocarb hydrochlorid, valiphenal and N-(1-(1-(4-cyano-phenyl)-ethanesulfonyl)-but-2-yl) carbamic acid-(4-fluorophenyl) ester;

F) other active substances selected from the group consisting of
guanidines: guanidine, dodine, dodine free base, guazatine, guazatine-acetate, iminoctadine, iminoctadine-triacetate, iminoctadine-tris(albesilate);
antibiotics: kasugamycin, kasugamycin hydrochloride-hydrate, streptomycin, polyoxine, validamycin A, streptomycin;
nitrophenyl derivates: binapacryl, dinobuton, dinocap, nitrthal-isopropyl, tecnazen,
organometal compounds: fentin salts, such as fentin-acetate, fentin chloride or fentin hydroxide;
sulfur-containing heterocyclyl compounds: dithianon, isoprothiolane;
organophosphorus compounds: edifenphos, fosetyl, fosetyl-aluminum, iprobenfos, phosphorous acid and its salts, pyrazophos, tolclofos-methyl;
organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;
inorganic active substances: Bordeaux mixture, copper acetate, copper hydroxide, copper oxychloride, basic copper sulfate, sulfur;
others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoronnethyl-phenoxy)-2,5-dinnethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester; fentin acetate, fentin chloride, fentin hydroxide;

G) plant growth regulators (PGRs) selected from the group consisting of abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

H) herbicides selected from the group consisting of
acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
amino acid derivatives: bilanafos, glufosinate, sulfosate;
aryloxyphenoxypropionates: clodinafop, cyhalofop-butyl, fenoxaprop, fluazifop, haloxyfop, metamifop, propaquizafop, quizalofop, quizalofop-P-tefuryl;
Bipyridyls: diquat, paraquat;
(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;
phenoxy acetic acids: clomeprop, 2,4-dichlorophenoxyacetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, methabenzthiazuron, tebuthiuron;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxy-ethoxymethyl)-6-trifluoromethyl-pyridine-3-carbonyl]-bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

J) insecticides selected from the group consisting of organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

All mixtures set forth above are also an embodiment of the present invention.

In one embodiment, the invention relates to the use of the *Bacillus subtilis* strain with NRRL Accession No. B-21661 or a cell-free extract thereof, and/or a mutant of this strain or extract having all the identifying characteristics of the respective strain or extract as component (I), and optionally of at least one chemical compound as component (II), selected from the active compound groups A) to J), for increasing the vigor and/or crop yield of agricultural plants under essentially non-existent pathogen pressure.

The below remarks as to preferred embodiments of component (I) as well as component (II) and respective mixtures and/or compositions comprising component (I) as well as component (II), to their preferred use and methods of using them are to be understood either each on their own or preferably in combination with each other.

In a preferred embodiment, the present invention relates to a method for increasing the vigor and/or crop yield of agricultural plants under essentially non-existent pathogen pressure, wherein the plants, the plant propagules, the seed of the plants and/or the locus where the plants are growing or are intended to grow are treated with an effective amount of a composition comprising a) the *Bacillus subtilis* strain with NRRL Accession No. B-21661 or a cell-free extract thereof, and/or a mutant of this strain or extract having all the identifying characteristics of the respective strain or extract as component (I), and b) one chemical compound as component (II), selected from the active compound groups A) to J) as defined above, in a weight ratio of from 100:1 to 1:100.

In another preferred embodiment, the present invention relates to a method for increasing the vigor and/or crop yield of agricultural plants under essentially non-existent pathogen pressure, wherein the plants, the plant propagules, the seed of the plants and/or the locus where the plants are growing or are intended to grow are treated with an effective amount of a composition comprising a) the *Bacillus subtilis* strain with NRRL Accession No. B-21661 or a cell-free extract thereof, and/or a mutant of this strain or extract having all the identifying characteristics of the respective strain or extract as component (I), and b) two chemical compounds as component (II), selected from the active compound groups A) to J) as defined above.

In another preferred embodiment, the present invention relates to a method for increasing the vigor and/or crop yield of agricultural plants under essentially non-existent pathogen pressure, wherein the plants, the plant propagules, the seed of the plants and/or the locus where the plants are growing or are intended to grow are treated with an effective amount of a composition comprising a) the *Bacillus subtilis* strain with NRRL Accession No. B-21661 or a cell-free extract thereof, and/or a mutant of this strain or extract having all the identifying characteristics of the respective strain or extract as component (I) and b) one chemical compound as component (II), selected from the active compound groups A) to J) as defined in claim 1 are applied simultaneously, that is jointly or separately, or in succession.

Component (I) embraces not only the isolated, pure cultures of the *Bacillus subtilis* strain or a cell-free extract thereof, but also their suspensions in a whole broth culture or a metabolite-containing supernatant or a purified metabolite obtained from a whole broth culture of the strain.

The *Bacillus subtilis* strain, extracts and mutants thereof, and the metabolites produced by this strain, its preparation and action against harmful fungi is known from WO 98/50422 and WO 00/29426, therein also referred to as AQ 713 (QST 713). Said strain, however, may also be referred to in the prior art as *Bacillus amyloliquefaciens*.

SERENADE® is a microbial biological control agent based on *Bacillus subtilis* which protects against fungal and bacterial plant pathogens. *Bacillus subtilis* strain QST 713 is a naturally occurring widespread bacterium that can be used to control plant diseases including blight, scab, gray mold, and several types of mildew. Regulatory authorities in USA and Europe classified *Bacillus subtilis* QST 713 as displaying no adverse effects on humans or the environment. The bacterium, *Bacillus subtilis*, is prevalent in soils and has been found in a variety of habitats worldwide. The QST 713 strain of *Bacillus subtilis* is known to be antagonistic towards many fungal plant pathogens.

This antagonism may be achieved in several ways including nutrient competition, site exclusion, colonization, and attachment of the bacteria to the fungal pathogen. In addition, the QST 713 strain of *Bacillus subtilis* might induce plant's natural systemic resistance or systemic acquired resistance (SAR) against bacterial pathogens. OST 713 can stop plant pathogen spores from germinating, disrupt germ tube growth, and inhibit attachment of the plant pathogen to the leaf.

Suitable formulations of the *Bacillus subtilis* strain with NRRL Accession No. B-21661 are commercially available under the tradenames SERENADE®, SERENADE® MAX and SERENADE® ASO from AgraQuest, Inc., 1540 Drew Avenue, Davis, Calif. 95618, U.S.A.

In one embodiment, a commercially available formulation of the above identified *Bacillus subtilis* strain is used.

A reduction of yield loss due to the control of fungal pathogens by component (I) is well known (see, for example Highland (2002): Proc. Fla. State Hort. Soc.: 115, 186-188).

In a presentation at the 2008 Acorbat conference, results were presented showing that when *Bacillus subtilis* QST 713, formulated as the SERENADE® product, was applied to black sigatoka-infected bananas, it controlled disease comparable to the chemical standard (mancozeb) resulting in an increased banana bunch production by 30% above the mancozeb-treated plots (see Manker and Seiler (2008): "*Bacillus subtilis* strain QST 713 as an Alternative Protectant Multi-Site Fungicide for Sustainable Control of Black Sigatoka in Banana Production" distributed Nov. 10, 2008 at Acorbat conference in Guayaquil, Ecuador).

However, the fact that the application of the *Bacillus subtilis* strain with NRRL Accession No. B-21661 or a cell-free extract thereof, and/or a mutant of this strain or extract having all the identifying characteristics of the respective strain or extract increases the vigor and/or the yield of agricultural plants even under essentially non-existant pathogen pressure is new and surprising because it could not have been expected that the yield and/or vigor increase would generally be above the level that could be reached by combating the phytopathogenic fungi and/or bacteria known to reduce a crop's vigor and yield. This is especially true with respect to the application of compositions comprising component (I) and at least one component (II) which have shown to be able to synergistically increase of a crop's vigor and yield according to the invention.

The term "essentially non-existant pathogen pressure" refers to a situation in which pathogens are present within the area of growth of a plant but in a quantity that is not harmful to the plant and which does neither result in a decrease of vigor nor in a decrease of yield.

In view of the increasing world population of humans, it becomes more and more important to increase the worldwide food production (yield) and food quality which is based upon healty plants that display high levels of vigor.

Accordingly, it was an object of the present invention to provide agents which increase the vigor and/or yield of plants to an extent which is more than healthy plants under essentially non-existent pathogen pressure would produce, whereas the term pathogen shall primarely mean fungal pathogens and optionally bacterial pathogens causing damage to plants, preferably both fungal and bacterial pathogens.

We have found that this object is achieved by applying component (I) and, optionally at least one component (II) as defined at the outset. In a preferred embodiment of the invention, component (I) and at least one component (II) as defined at the outset, are applied. By simultaneous, that is joint or separate, application of component (I) and at least one component (II), the vigor and/or the yield of agricultural plants may be increased in a superadditive that means synergistic manner.

The concept of using biopesticides such as a SERENADE® product in combination with chemicals is new and has a number of benefits. One of the most important is the fact that biopesticides such as SERENADE® don't leave any chemical residues on the crops, meaning that they can be used right up to the day of harvest. Crops are usually left perilously unprotected in the days leading up to harvest, as conventional pesticides cannot be applied during this time. Accordingly, in a preferred embodiment of the method according to the invention, at least one component (II) selected from the active compound groups (A) to (J) are applied before the Pre-Harvest Intervall while compond (I) is applied during the Pre-Harvest Intervall.

The term "Pre-Harvest Interval" is to be understood as the time between the last pesticide application (component II) and harvest of the treated crops.

The term "principal growth stage" refers to the extended BBCH-scale which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry. A BBCH value of 23/29 indicates that the plants measured had reached a growing stadium in between 23 and 29.

NRRL is the abbreviation for the Agricultural Research Service Culture Collection, an international depositary authority for the purposes of deposing microorganism strains under the BUDAPEST TREATY ON THE INTERNATIONAL RECOGNITION OF THE DEPOSIT OF MICROORGANISMS FOR THE PURPOSES OF PATENT PROCEDURE, having the address National Center for Agricultural Utilization Research, Agricultural Research Service, U.S. Department of Agriculture, 1815 North University Street, Peoria, Ill. 61604, USA.

Component (I) embraces not only the isolated, pure cultures of the *Bacillus subtilis* strain, but also its suspensions in a whole broth culture or as a metabolite-containing supernatant or a purified metabolite obtained from a whole broth culture of the strain.

"Whole broth culture" refers to a liquid culture containing both cells and media.

"Supernatant" refers to the liquid broth remaining when cells grown in broth are removed by centrifugation, filtration, sedimentation, or other means well known in the art.

The term "metabolite" refers to any compound, substance or byproduct produced by a microorganism (such as fungi and bacteria) that has fungicidal activity.

The chemical compounds mentioned above as component (II) are generally known (cf., for example, http://www.hcl-rss.demon.co.uk/index.html); most of them are commercially available. Their pesticidal action and methods for producing them are also known. For instance, the commercially available compounds may be found in The Pesticide Manual, 14th Edition, British Crop Protection Council (2006) among other publications.

Bixafen is known from WO 03/070705; penflufen is known from WO 03/010149; Sedaxane is known from WO 03/074491; they can be prepared in the manner described therein. Isopyrazam is known from WO 04/035589 and can be prepared in the manner described therein or as described in WO 2007/068417. N-(3',4',5'-trifluorobiphenyl-2-yl)-3-difluoromethyl-1-methyl-1H-pyrazole-4-carboxamide is known from WO 06/087343 and can be prepared in the manner described therein. Metrafenone, 3'-bromo-2,3,4,6'-tetramethoxy-2',6-dimethylbenzophenone, is known from U.S. Pat. No. 5,945,567.

The compounds according to the invention can be present in different crystal modifications whose biological activity may differ. They are likewise subject matter of the present invention.

Preference is given to the application of component (I) in combination with at least one component (II).

Accordingly, in a preferred embodiment of the method according to the invention, component (I) is applied together with a component (II) selected from the groups A), B), C), D), E), F) and G). In a more preferred embodiment of the method according to the invention, component (I) is applied together with a component (II) selected from the groups A), B), C), E) and G). In an even more preferred embodiment of the method according to the invention, component (I) is applied together with a component (II) selected from the groups A) and B). In a most preferred embodiment of the method according to the invention, component (I) is applied together with a component (II) selected from the group A).

In one embodiment of the method according to the invention, component (I) is applied together with a component (II) selected from group A) (strobilurins) consisting of azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxy¬imino-N-methyl-acetamide, 3-methoxy-2-(2-(N-(4-methoxy-phenyl)-cyclopropane-carboximidoyl¬sulfanylmethyl)-phenyl)-acrylic acid methyl ester, methyl(2-chloro-5[1-(3-methylbenzyloxyimino)¬ethyl]benzyl)¬carbamate and 2(2-(3-(2,6-di¬chlorophenyl)-1-methyl-allylidene¬aminooxy¬methyl)-phenyl)-2-methoxyimino-N methyl-acetamide. Among the group A) comprising strobilurins as component (II), azoxystrobin, dimoxystrobin, enestroburin, fluoxastrobin, kresoxim-methyl, orysastrobin, picoxystrobin, pyraclostrobin and trifloxystrobin are preferred. Azoxystrobin, dimoxystrobin, and pyraclostrobin are especially preferred. Pyraclostrobin is most preferred.

In a especially preferred embodiment of the invention, component (I) is applied with pyraclostrobin as component (II).

In another especially preferred embodiment of the invention, component (I) is applied with epoxiconazole and pyraclostrobin as component (II).

In another embodiment of the method according to the invention, component (I) is applied together with a component (II) selected from group B) (carboxamides) consisting of carboxanilides selected from benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2 chloro-N(1,1,3-trimethylindan-4-yl)-nicotinamide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H-pyrazole-4-carboxamide, N(2-(1,3 dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4 carboxamide;

carboxylic morpholides selected from dimethomorph, flumorph and pyrimorph;
benzoic acid amides selected from flumetover, fluopicolide, fluopyram, zoxamide and N-(3-Ethyl-3,5,5-trimethyl-cyclohexyl)-3-formylamino-2-hydroxy-benzamide;
other carboxamides selected from carpropamid, diyclomet, mandiproamid, oxytetracyclin, silthiofarm and N-(6-methoxy-pyridin-3-yl)cyclopropanecarboxylic acid amide.

Among the group B) comprising carboxamides as component (II), carboxanilides, carboxylic morpholides and benzoic acid amides are preferred. Within the group of carboxanilides, bixafen, boscalid and N-(3',4',5'-trifluorobiphenyl-2-yl)-3-difluoromethyl-1-methyl-1H-pyrazole-4-carboxamide are especially preferred. Within the group of carboxylic morpholides, dimethomorph and flumorph are especially preferred. Within the group of benzoic acid amides, zoxamide is especially preferred. Bixafen, boscalid and N-(3',4',5'-trifluorobiphenyl-2-yl)-3-difluoromethyl-1-methyl-1H-pyrazole-4-carboxamide are even more preferred. N-(3',4',5'-trifluorobiphenyl-2-yl)-3-difluoromethyl-1-methyl-1H-pyrazole-4-carboxamide is most preferred.

In a especially preferred embodiment of the invention, component (I) is applied with boscalid as component (II). In another especially preferred embodiment of the invention, component (I) is applied with N-(3',4',5'-trifluorobiphenyl-2-yl)-3-difluoromethyl-1-methyl-1H-pyrazole-4-carboxamide as component (II).

In another embodiment of the method according to the invention, component (I) is applied together with a component (II) selected from group C) (azoles) consisting of
triazoles selected from azaconazole, bitertanol, bromuconazole, cyproconazole, difenoconazole, diniconazole, diniconazole-M, epoxiconazole, fen-buconazole, fluquinconazole, flusilazole, flutriafol, hexaconazole, imibenconazole, ipconazole, metconazole, myclobutanil, oxpocona-zole, paclobutrazole, penconazole, propiconazole, prothioconazole, simeconazole, tebuconazole, tetraconazole, triadimefon, triadimenol, triticonazole, uniconazole and 1-(4-chloro-phenyl)-2-([1,2,4]triazol-1-yl)-cycloheptanol;
imidazoles selected from cyazofamid, imazalil, pefurazoate, prochloraz and triflumizol;
benzimidazoles selected from benomyl, carbendazim, fuberidazole and thiabendazole;
others selected from ethaboxam, etridiazole, hymexazole and 2-(4-chlorophenyl)-N-[4-(3,4-dimethoxy-phenyl)-isoxazol-5-yl]-2-prop-2-ynyloxy-acetamide.

Among group C) comprising azoles as component (II), triazoles, imidazoles, benzimidazoles and ethaboxam are preferred. Within the group of triazoles, bitertanol, cyproconazole, difenoconazole, epoxiconazole, fenbuconazole, fluquinconazole, flusilazole, flutriafol, hexaconazole, metconazole, myclobutanil, propiconazole, tebuconazole and triticonazole are especially preferred. Within the group of imidazole, cyazofamid and prochloraz are especially preferred. Within the group of benzimidaoles, benomyl, carbendazim and thiabendazole are especially preferred. Within group C), cyproconazole, difenoconazole, epoxiconazole and tebuconazole are especially preferred. Epoxiconazole is most preferred.

In an especially preferred embodiment of the invention, component (I) is applied with epoxiconazole as component (II).

In another especially preferred embodiment of the invention, component (I) is applied with difenoconazole and mefenoxam as component (II).

In another embodiment of the method according to the invention, component (I) is applied together with a component (II) selected from the group D) (heterocyclic compounds) consisting of
pyridines selected from fluazinam, pyrifenox, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide and N[(5 bromo-3-chloro-pyridin-2-yl)-methyl]-2,4-dichloro-nicotinamide;
pyrimidines selected from bupirimate, cyprodinil, diflumetorim, fenarimol, ferimzone, mepanipyrim, nitrapyrin, nuarimol, pyrimethanil;
piperazines: triforine;
pyrroles selected from fenpiclonil and fludioxonil;
morpholines selected from aldimorph, dodemorph, dodemorph-acetate, fen-propimorph and tridemorph;
piperidines: fenpropidin;
dicarboximides selected from fluoroimid, iprodione, procymidone and vinclozolin;
non-aromatic 5-membered heterocycles selected from famoxadone, fenamidone, flutianil, octhilinone, probenazole and 5-amino-2-isopropyl-3-oxo-4-orthotolyl-2,3-dihydro-pyrazole-1 carbothioic acid S-allyl ester;
others selected from acibenzolar-S-methyl, amisulbrom, anilazin, blasticidin-S, captafol, captan, chinomethionat, dazomet, debacarb, diclomezine, difenzoquat, difenzoquat-methyl¬sulfate, fenoxanil, Folpet, oxolinic acid, piperalin, proquinazid, pyroquilon, quin¬oxyfen, triazoxide, tricy-clazole, 2-butoxy-6-iodo-3-propylchromen-4-one, 5-chloro-1 (4,6-dimethoxy-pyrimidin-2-yl)-2-methyl-1H-benzoimidazole, 5 chloro-7 (4-methyl¬piperidin-1-yl)-6-(2,4,6-trifluorophenyl)-[1,2,4]triazolo¬[1,5 a]pyrimidine and 5-ethyl-6 octyl-[1,2,4]triazolo[1,5-a]pyri¬midine-7 ylamine.

Among group D) comprising heterocyclic compounds as component (II), pyridines, pyrimidines, morpholines, piperidines, dicarboximides and non-aromatic 5-membered heterocycles are preferred. Within the group of pyridines, fluazinam is especially preferred. Within the group of pyrimidines, cyprodinil, fenarimol and pyrimethanil are especially preffered. Within the group of morpholines, dodemorph-acetate, fenpropimorph and tridemorph are especially preferred. Within the group of piperidines, fenpropidin is especially preferred. Within the group of dicarboximides, iprodione is especially preferred. Within the group of non-aromatic 5-membered heterocycles famoxadone and fenamidone are especially preferred. In addition, samisulbrom, Folpet, proquinazid and quinoxyfen are especially preferred. Cyprodinil, fenpropidin, iprodione, famoxadone, fenamidone, amisulbrom, proquinazid, quinoxyfen and Folpet are even more preferred. Fenpropimorph, tridemorph and fenpropidin are most peferred.

In another embodiment of the method according to the invention, component (I) is applied together with a component (II) selected from group E) (carbamates) consisting of
thio- and dithiocarbamates selected from ferbam, mancozeb, maneb, metam, methasulphocarb, metiram, propineb, thiram, zineb and ziram;

carbamates selected from benthiavalicarb, diethofencarb, iprovalicarb, propamo-carb, propamocarb hydrochlorid, valiphenal and N-(1-(1-(4-cyano-phenyl)¬ethanesulfonyl)-but-2-yl)carbamic acid-(4-fluorophenyl)ester.

Among group E) comprising carbamates as component (II), thio- and dithiocarbamates and carbamates are preferred. Within the group of thio- and dithiocarbamates, mancozeb, maneb, metiram, propineb, thiram, zineb and ziram are more preferred. Within the group of carbamates, benthiavalicarb, iprovalicarb, valiphenal and propamocarb and valiphenal are preferred. Mancozeb, metiram and propineb are even more preferred.

In another embodiment of the method according to the invention, component (I) is applied together with a component (II) selected from the group F). Among the group F) comprising other active substances as component (II), antibiotics, sulfur-containing heterocyclyl compounds, inorganic active substances, cymoxanil, metrafenone, spiroxamine fentin acetate, fentin chloride and fentin hydroxide are preferred. Within the group of antibiotics, kasugamycin, kasugamycin hydrochloride-hydrate and streptomycin are especially preferred. Within the group of sulfur-containing heterocyclyl compounds, dithianon is especially preferred. In addition, cymoxanil, metrafenone, spiroxamine, fentin acetate, fentin chloride, fentin hydroxide are preferred. Inorganic active substances selected from Bordeaux mixture, copper acetate, copper hydroxide, copper oxychloride, basic copper sulfate and sulfur are especially preferred.

In an especially preferred embodiment of the invention, component (I) is applied together with component (II) selected from Bordeaux mixture, copper acetate, copper hydroxide, copper oxychloride, basic copper sulfate and sulfur.

In another embodiment of the method according to the invention, component (I) is applied together with a component (II) selected from group G) (plant growth regulators; PGRs) consisting of abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole. Among the group G) comprising plant growth regulators (PGRs) as component (II), chlormequat (chlormequat chloride), mepiquat (mepiquat chloride and prohexadione (prohexadione-calcium) are preferred.

One indicator for the condition of the plant is its yield. "Yield" is to be understood as any plant product of economic value that is produced by the plant such as grains, fruits in the proper sense, vegetables, nuts, grains, seeds, wood (e.g. in the case of silviculture plants) or even flowers (e.g. in the case of gardening plants, ornamentals). The plant products may in addition be further utilized and/or processed after harvesting.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the invention. Increased yield can be characterized, among others, by following improved properties of the plant:
increased plant weight,
increased plant height,
increased biomass such as higher fresh and/or dry weight
higher grain yield
more tillers
larger leaves
increased shoot growth
increased protein content
increased oil content
increased starch content
increased pigment content According to one embodiment of the present invention, the yield is increased by at least 5%. According to another embodiment of the present invention, the yield is increased by least 10%. According to another embodiment of the present invention, the yield is increased by least 15%. According to another embodiment of the present invention, the yield is increased by least 30%. According to another embodiment of the present invention, the yield is increased by least 40%.

Another indicator for the condition of the plant is the "plant vigor". The plant vigor becomes manifest in several aspects such as the general visual appearance. Improved plant vigor can be characterized, among others, by following improved properties of the plant:
improved vitality of the plant,
improved plant growth,
improved plant development,
improved visual appearance,
improved plant stand (less plant verse/lodging),
improved emergence,
enhanced root growth and/or more developed root system,
enhanced nodulation, in particular rhizobial nodulation,
bigger leaf blade,
increased plant size,
increased plant weight,
increased plant height,
increased tiller number,
increased shoot growth,
increased root growth (extensive root system),
increased size of root mass (extensive root system),
increased yield when grown on poor soils or unfavorable climate,
enhanced photosynthetic activity
change of color (e.g. enhanced pigment content (e.g. Chlorophyll content)
earlier flowering,
earlier fruiting,
earlier and improved germination,
earlier (advanced) grain maturity,
improved self-defence mechanisms
less non-productive tillers,
less dead basal leaves,
less input needed (such as fertilizers or water)
greener leaves and increased green leaf area
complete maturation under shortened vegetation periods
less fertilizers needed,
less seeds needed,
easier harvesting
faster and more uniform ripening
longer shelf-life
longer panicles
delay of senescence,
stronger and/or more productive tillers, better extractability of ingredients
improved quality of seeds (for being seeded in the following seasons for seed production)
reduced production of ethylene and/or the inhibition of its reception by the plant
spindliness of leaves
inceased number of ears/m²

The improvement of the plant vigor according to the present invention particularly means that the improvement of any one or several or all of the above mentioned plant characteristics are improved independently of the pesticidal action of the composition or active ingredients. An increased vigor may for example result in a higher percentatage of plants that can be transplanted to the field or an increased number of marketable plants (such as tomatoes).

The term "plants" is to be understood as plants of economic importance and/or men-grown plants such as cultivated plants. They are preferably selected from agricultural, silvicultural and horticultural (including ornamental) plants. The term "plant" as used herein includes all parts of a plant such as germinating seeds, emerging seedlings, herbaceous vegetation as well as established woody plants including all belowground portions (such as the roots) and aboveground portions.

Generally the term "plants" also includes plants which have been modified by breeding, mutagenesis or genetic engineering. Genetically modified plants are plants, which genetic material has been modified by the use of recombinant DNA techniques. The use of recombinant DNA techniques makes modifications possible that cannot readily be obtained by cross breeding under natural circumstances, mutations or natural recombination.

Agricultural plants which may exhibit an increase in vigor and/or crop yield are, for example, cereals, for example wheat, rye, barley, triticale, oats or rice; beet, for example sugar beet or fodder beet; fruits, such as pomes, stone fruits or soft fruits, for example apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as broccoli, spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, for example conifers; and on the plant propagation material, such as seeds, and the crop material of these plants.

Agricultural plants which exhibit vigor and/or crop yield increase are in particular bananas, broccoli, tomatoes, pepper and wheat.

In a preferred embodiment of the invention, the yield and/or vigor is increased in an agricultural plant selected from soybean, corn, wheat, triticale, barley, oat, rye, rape, millet, rice, sunflower, cotton, sugar beet, pome fruit, stone fruit, citrus, banana, strawberry, blueberry, almond, grape, mango, papaya, peanut, potato, tomato, pepper, cucurbit, cucumber, melon, watermelon, garlic, onion, broccoli, carrot, cabbage, bean, dry bean, canola, pea, lentil, alfalfa, trefoil, clover, flax, elephant grass, grass, lettuce, sugarcane, tea, tobacco and coffee; each in its natural or genetically modified form In a preferred embodiment of the invention, the yield and/or vigor is increased in grapes, fruits such as pomes, stone fruits or soft fruits, for example apples, pears, plums, peaches, almonds, cherries, strawberries, raspberries, blackberries or gooseberries and/or vegetables such as broccoli, spinach, lettuce, asparagus, cabbages, carrots, onions, tomatoes, potatoes, cucurbits or paprika.

In an especially preferred embodiment of the invention, the yield and/or vigor is increased in bananas and/or grapes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be treated totally or partially by immersion or pouring before transplantation.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant.

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically modified plants capable of synthesizing such toxins are disclosed, for example, in EP-A374753, WO 93/007278, WO 95/34656, EP-A 427529, EP-A451878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda).

Genetically modified plants capable to synthesize one or more insecticidal proteins are, for example, described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0392225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. biomass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

The term "protein" as used herein is to be understood as an oligopeptide or polypeptide or molecule made up of polypeptides including expressly also pre-proteins, hybrid proteins, peptides, truncated or otherwise modified proteins including those derived from post-transcriptional modifications such as acylation (e.g. acetylation, the addition of an acetyl group, usually at the N-terminus of the protein), alkylation, the addition of an alkyl group (e.g. addition of ethyl or methyl, usually at lysine or arginine residues) or demethylation, amidation at C-terminus, biotinylation (acylation of conserved lysine residues with a biotin appendage), formylation, γ-carboxylation dependent on Vitamin K, glutamylation (covalent linkage of glutamic acid residues), glycosylation (addition of a glycosyl group to either asparagine, hydroxylysine, serine, or threonine, resulting in a glycoprotein), glycation (nonenzymatic attachment of sugars), glycylation (covalent linkage of one to more glycine residues), covalent attachment of a heme moiety, hydroxylation, iodination, isoprenylation (addition of an isoprenoid group such as farnesol and geranylgeraniol), lipoylation (attachment of a lipoate functionality) including prenylation, GPI anchor formation (e.g. myristoylation, farnesylation and geranylgeranylation), covalent attachment of nucleotides or derivatives thereof including ADP-ribosylation and flavin attachment, oxidation, pegylation, covalent attachment of phosphatidylinositol, phosphopantetheinylation (addition of a 4'-phosphopantetheinyl moiety from coenzyme A), phosphorylation (addition of a phosphate group, usually to serine, tyrosine, threonine or histidine), pyroglutamate formation, racemization of proline, tRNA-mediated addition of amino acids such as arginylation, sulfation (addition of a sulfate group to a tyrosine), selenoylation (co-translational incorporation of selenium in selenoproteins), ISGylation (covalent linkage to the ISG15 protein [Interferon-stimulated Gene 15]), SUMOylation (covalent linkage to the SUMO protein [Small Ubiquitin-related MOdifier]), ubiquitination (covalent linkage to the protein ubiquitin or polyubiquitin), citrullination or deimination (conversion of arginine to citrulline), deamidation (conversion of glutamine to glutamic acid or asparagine to aspartic acid), formation of disulfide bridges (covalent linkage of two cysteine amino acids) or proteolytic cleavage (cleavage of a protein at a peptide bond).

The term "locus" is to be understood as any type of environment, soil, area or material where the plant is growing or intended to grow as well as the environmental conditions (such as temperature, water availability, radiation) that have an influence on the growth and development of the plant and/or its propagules. In addition, the term "locus" is to be understood as a plant, seed, soil, area, material or environment in which a pest is growing or may grow.

"Crop yield" is an indicator for the condition of the plant, whereas "crop" is to be understood as any plant or plant product which is further utilized after harvesting, e.g. fruits in the proper sense, vegetables, nuts, grains, seeds, wood (e.g. in the case of silviculture plants), flowers (e.g. in the case of gardening plants, ornamentals) etc., that is anything of economic value that is produced by the plant.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the invention.

The term "seed" embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "seed treatment" comprises all suitable seed treatment techniques known in the art, such as seed dressing, seed coating, seed dusting, seed soaking, seed impregnation and seed pelleting.

The term "plant propagation material" or "plant propagation product" is to be understood to denote all the generative parts of the plant such as seeds and vegetative plant material such as cuttings and tubers (e.g. potatoes), which can be used for the multiplication of the plant. This includes seeds, grains, roots, fruits, tubers, bulbs, rhizomes, cuttings, spores, offshoots, shoots, sprouts and other parts of plants, including seedlings and young plants, which are to be transplanted after germination or after emergence from soil, meristem tissues, single and multiple plant cells and any other plant tissue from which a complete plant can be obtained.

The term "coated with" and/or "containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

A "simultaneous" application is to be understood as the joint or separate application of components (I) and (II).

Component (I) may be formulated with a particulate carrier substance. Said carrier may be substantially composed of water-soluble or water-insoluble material or mixtures thereof. The *Bacillus subtilis* cells may be embedded into the carrier material and/or may be adsorbed to the surface of the carrier material.

The carrier substance, which may added as coformulant prior to the drying to a suspension of usually freshly grown of the *Bacillus subtilis* cells, may be selected from mono-, oligo- and polysaccharides, polyols, polyethers, polymers, such as CMC or PVP, oligo- and polypeptides, from natural sources, such as milk, meat or cereals, derived substances or mixed substances, such as sweet whey powder, wheat semolina bran, peptone, alginates, mineral compounds, or mixtures of such materials. Said material may be dissolved in said suspension of *Bacillus subtilis* cells, which mxture may then be dried in order to obtain particulate material.

In another embodiment, said carrier may comprise a water insoluble, water-absorbent carrier substance, which may be is selected from any organic or inorganic material capable of removing moisture gently from the suspension of viable *Bacillus subtilis*, and in particular from the group consisting of zeolite, porous beads or powders, silica, ground agricultural products (as for example corn cobs), porous wood products, cellulose, cyclodextrins, and combinations thereof. The carrier may be admixed with a suspension of usually freshly grown of *Bacillus subtilis* cells in order to form particulate material, which optionally my be further subjected to drying.

In addition, additives having a stabilizing action on the *Bacillus subtilis* can be added to the mixture, preferably prior to the preparation of the particulate formulation, as for example antioxidants, such as alpha-tocopherol or ascorbic acid, or mixtures thereof. Furthermore, a stabilizing action can be exerted by other substances, which are selected from inorganic salts, such as alkali metal chlorides or alkaline earth metal chlorides, inorganic or organic buffers, such as alkali metal phosphate buffer, amino acids, such as aspartic acid or glutamic acid and the salts thereof, organic carboxylic acids, such as citric acid, organic nonvolatile solvents, such as dimethylsulfoxide, and other compounds, such as β-carotene and mixtures of these.

In a specific embodiment the particulate formulation comprises said carrier substance, as for example said water insoluble, water-absorbent carrier substance, wherein said carrier substance is present in an amount of at least about 40%, as for example at lease 50, 60, 70, 80, 85, 90, 95, 96, 97, 98 or 99% by the total weight of the formulation and the *Bacillus subtilis* mixed with said carrier.

According to a further embodiment said particulate formulation is coated in a manner known per se with a suitable compatible coating or encapsulating material.

Suitable encapsulating materials include, without limitation, native or modified chitosans, native of modified starches, glucans or dextrins, celluloses modified so they are soluble, and any of a number of native or modified vegetable or microbial gums, including agars, guar, locust, carrageenan, xanthans, pectins, and the like, and combinations thereof.

Further suitable coating materials are polymers such as, for example, PVP, in particular a PVP product, which is commercially available under the trade name Kollidon VA64. Another usable coating system comprises a mixture of shellac and Kollidon 25 or 30, which may be supplemented with titanium dioxide and tallow.

According to the invention, components (I) and (II) are usually employed in a weight ratio of from 1000:1 to 1:1000, as for example 200:1 to 1:200, 100:1 to 1:100, as for example 90:1 to 1:90, 80:1 to 1:80, 75:1 to 1:75, 50:1 to 1:50, 25:1 to 1:25 or 10:1 to 1:10.

It is preferred to employ the commercially available formulations of components (I) and (II), to which further compounds active against harmful fungi or other pests, such as insects, arachnids or nematodes, or else herbicidal or growth-regulating active compounds (e.g. PGRs), fertilizers or sun protectants like iron oxide may be added. In a preferred embodiment, the composition comprises component (I), at least one component (II) and iron oxide.

The further active components (II) are, if desired, added in a ratio of from 20:1 to 1:20 to component (I).

Usually, compositions comprising component (I) and (II), wherein component (II) consists of only one chemical compound, are employed. However, in certain cases compositions wherein component (II) consists of two or, if appropriate, more chemical compounds may be advantageous as well.

According to the terms of the present invention, "effective amount" is to be understood to denote all application rates for component (I) and optionally component (II) as well as all application rates with regard to any type of mixture or composition comprising component (I) and at least one component (II), which result in an increased vigor and/or crop yield of agricultural plants under essentially non-existent pathogen pressure. The optimal "effective amount" depends on various parameters such as the time of application, growth stage, area of application, application form, treated plant, soil, weather conditions etc. and must be determined by the person skilled in the art withing the ranges given.

In one embodiment of the method according to the invention, mixtures comprising component (I) and at least one component (II) are applied in an effective amount, whereas "effective amount" is to be understood as an amount suitable for increasing the vigor and/or crop yield of agricultural plants under essentially non-existent pathogen pressure in a synergistic manner.

Depending on the particular components and the plants to be treated, the application rates for component (I) in liquid formulations are generally from 0.01 l to 100 l of a composition containing the *Bacillus subtilis* strain or a mutant having all the identifying characteristics of such strain, a cell-free extract of the strain or its mutants, or isolated metabolite(s) of the strain or its mutant per hectare, preferably from 0.02 l to 50 l/ha, in particular from 0.05 to 18 l/ha. Application rates for component (I) in dry formulations are generally from 0.01 lbs/acre to 100 lbs/acre, preferably from 0.02 lbs to 50 lbs per acre and in particular from 0.05 lbs to 5 lbs/acre. In cases in which component (I) is derived from a whole broth of the *Bacillus subtilis* strain or its mutants the number of colony forming units (CFU) applied is important and is generally from $1 \times 10^{10}$ through $1 \times 10^{15}$ per acre, preferably from $1 \times 10^{11}$ through $1 \times 10^{14}$ per acre or, in particular from $1 \times 10^{12}$ through $1 \times 10^{13}$ per acre.

Correspondingly, the application rates for component (II) are generally from 1 to 2000 g/ha, 5 to 100 g/ha, preferably from 10 to 500 g/ha, in particular from 40 to 250 g/ha of active ingredient each.

Correspondingly, the application rates for component (II) are generally from 1 to 2000 g/ha, preferably from 10 to 1500 g/ha, in particular from 40 to 1000 g/ha.

In a preferred embodiment of the method according to the invention, seed is treated.

The method according to the present invention is carried out by the application of a component (I) and optionally a component (II), or a composition comprising components (I) and optionally a component (II), by spraying or dusting the seeds, the plants or the soils before or after sowing of the plants or before or after emergence of the plants.

In a preferred method according to the present invention the application is carried out as in-furrow and/or foliar treatment. Most preferably, the application is carried out as foliar treatment.

If an agricultural mixture according to the present invention is used in this inventive method, the plants, the plant propagules, the seed of the plants and/or the locus where the plants are growin or are intended to grow are preferably treated simultaneously (together or separately) or subsequently with a compenent (I) and at least one compent (II) selected from the active compound groups (A) to (J).

The subsequent application is carried out with a time interval which allows a combined action of the applied compounds. Preferably, the time interval for a subsequent application of component (I) and at least one component (II), ranges from a few seconds up to 3 months, preferably, from a few seconds up to 1 month, more preferably from a few seconds up to 2 weeks, even more preferably from a few seconds up to 3 days and in particular from 1 second up to 24 hours.

In a preferred embodiment, component (II) is applied before the Pre-harvest interval while component (I) is applied during the Pre-harvest interval.

Herein, we have found that simultaneous, that is joint or separate, application of component (I), or mixtures comprising component (I) and at least one compound selected from the active compound groups (A) to (J) or the successive application of mixtures comprising component (I), or mixtures comprising component (I) and at least one compound selected from the active compound groups (A) to (J) allows increasing the vigor and/or crop yield of agricultural plants under essentially non-existent pathogen pressure compared to the control rates that are possible with the individual compounds (synergistic mixtures).

In another preferred embodiment of the invention, component (I) or an agrochemical mixture comprising component (I) and at least one compound selected from the active compound groups (A) to (J) is repeatedly applied. In one embodiment, the application is repeated two to ten times, preferably, two to five times; most preferably three times.

The compositions according to the invention, or the single components separately, can be converted into customary formulations, for example solutions, emulsions, suspensions, dusts, powders, pastes and granules. The use form depends on the particular intended purpose; in each case, it should ensure a fine and even distribution of the mixture according to the invention.

The formulations are prepared in a known manner, for example by extending the single components with solvents and/or carriers, if desired using emulsifiers and dispersants. Solvents/auxiliaries suitable for this purpose are essentially:

water, aromatic solvents (for example Solvesso® products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In order to achieve good dispersion and adhesion of compositions within the present invention, it may be advantageous to formulate the whole broth culture, supernatant and/or metabolite with components that aid dispersion and adhesion.

In general, the formulations comprise from 0.01 to 95% by weight, preferably from 0.1 to 90% by weight, of the components.

The chemical component (II) is employed in a purity of from 90% to 100%, preferably 95% to 100% (according to NMR spectrum).

The following are examples of formulations:

1. Products for Dilution with Water

A) Water-Soluble Concentrates (SL)

10 parts by weight of a composition according to the invention are dissolved in 90 parts by weight of water or in a water-soluble solvent. As an alternative, wetting agents or other auxiliaries are added. Dilution with water results in a formulation having a content of 10% by weight of components (I) and (II) is obtained.

B) Dispersible Concentrates (DC)

20 parts by weight of a composition according to the invention are dissolved in 70 parts by weight of cyclohexanone with addition of 10 parts by weight of a dispersant, for example polyvinylpyrrolidone. Dilution with water gives a dispersion having a content of 0% by weight of components (I) and (II).

C) Emulsifiable Concentrates (EC)

15 parts by weight of a composition according to the invention are dissolved in 75 parts by weight of xylene with addition of calcium dodecylbenzenesulfonate and castor oil ethoxylate (in each case 5 parts by weight). Dilution with water gives an emulsion. The formulation has a content of 15% by weight of components (I) and (II).

D) Emulsions (EW, EO)

25 parts by weight of a composition according to the invention are dissolved in 35 parts by weight of xylene with addition of calcium dodecylbenzenesulfonate and castor oil ethoxylate (in each case 5 parts by weight). This composition is introduced into 30 parts by weight of water by means of an emulsifying machine (Ultraturrax) and made into a homogeneous emulsion. Dilution with water gives an emulsion. The formulation has a content of 25% by weight of components (I) and (II).

E) Suspensions (SC, OD)

In an agitated ball mill, 20 parts by weight of a composition according to the invention are comminuted with addition of 10 parts by weight of dispersants and wetting agents and 70 parts by weight of water or an organic solvent to give a fine suspension. Dilution with water gives a stable suspension having a content of 20% by weight of components (I) and (II).

F) Water-Dispersible Granules and Water-Soluble Granules (WG, SG)

50 parts by weight of a composition according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution having a content of 50% by weight of components (I) and (II).

G) Water-Dispersible Powders and Water-Soluble Powders (WP, SP)

75 parts by weight of a composition according to the invention are ground in a rotor-stator mill with addition of 25 parts by weight of dispersants, wetting agents and silica gel. Dilution with water gives a stable dispersion or solution having a content of 75% by weight of components (I) and (II).

2. Products to be Applied Undiluted

H) Dustable Powders (DP)

5 parts by weight of a composition according to the invention are ground finely and mixed intimately with 95 parts by weight of finely divided kaolin. This gives a dustable product having a content of 5% by weight of components (I) and (II).

J) Granules (GR, FG, GG, MG)

0.5 part by weight of a composition according to the invention is ground finely and associated with 99.5 parts by weight of carriers. Current methods are extrusion, spray-drying or the fluidized bed. This gives granules to be applied undiluted having a content of 0.5% of weight of components (I) and (II).

K) ULV Solutions (UL)

10 parts by weight of a composition according to the invention are dissolved in 90 parts by weight of an organic solvent, for example xylene. This gives a product to be applied undiluted having a compound content of 10% by weight of components (I) and (II).

Components (I) and (II) can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of components (I) and (II) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The concentrations of the components in the ready-to-use preparations can be varied within relatively wide ranges. In general, they are from 0.0001 to 100%, preferably from 0.01 to 100%.

Components (I) and (II) may also be used successfully in the ultra-low-volume process (ULV), it being possible to apply formulations comprising over 95% by weight of active compound, or even to apply components (I) and (II) without additives.

Oils of various types, sun protectants, wetting agents or adjuvants may be added to the component (I) or (II), even, if appropriate, not until immediately prior to use (tank mix). These agents are typically admixed with component a) or b) according to the invention in a weight ratio of from 1:100 to 100:1, preferably from 1:10 to 10:1.

In one embodiment, component (I) is applied together with a sun protectant. Suitable sun protectants are, for example iron oxide or organic UV photoprotective filters.

Organic UV photoprotective filters are understood as meaning organic substances which are able to absorb ultraviolet rays and give off the absorbed energy again in the form of longer-wave radiation, e.g. heat. The term "Organic UV photoprotective filter" relates to one type or a mixture of different types of said compounds. The organic substances may be oil-soluble or water-soluble or they may be bound to a polymer. The photoprotective filters may be UV-A and/or UV-B filters, preferably UV-B filters.

UV-B filters which may be used are, for example, the following substances:

3-benzylidenecamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, isopentyl 4-methoxycinnamate, 2-ethylhexyl 2-cyano-3-phenylcinnamate (otocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 2-ethylhexyl 4-methoxybenzmalonate;

triazine derivatives, such as 2,4,6-trianilino(p-carbo-2'-ethyl-1'-hexyloxy)-1,3,5-triazine (octyltriazone) and dioctylbutamidotriazone (Uvasorb® HEB).

Propane-1,3-diones, such as, for example, 1-(4-tert-butylphenyl)-3-(4'-methoxyphenyl)propane-1,3-dione.

2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Preferred UV-B filters are derivatives of benzophenone.

Suitable UV-A filters are:

derivatives of benzoylmethane, for example 1-(4'-tert-butylphenyl)-3-(4'-methoxy-phenyl)propane-1,3-dione, 4-tert-butyl-4'-methoxydibenzoylmethane or 1-phenyl-3-(4'-isopropylphenyl)propane-1,3-dione;

Aminohydroxy-substituited derivatives of benzophenones, for example N,N-diethylaminohydroxybenzoyl-n-hexylbenzoate.

Suitable adjuvants in this sense are in particular: organically modified polysiloxanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

For seed treatment purposes, respective formulations can in certain cases be diluted 2-10 fold leading to concentrations in the ready to use preparations of 0.01 to 60% by weight active compound by weight, preferably 0.1 to 40% by weight.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In one embodiment a FS formulation is used for seed treatment. Typcially, a FS formulation may comprise 1-800 g/l of active ingredient, 1-200 g/l surfactant, 0 to 200 g/l anti-freezing agent, 0 to 400 g/l of binder, 0 to 200 g/l of a pigment and up to 1 liter of a solvent, preferably water.

In accordance with one variant of the present invention, a further subject of the invention is a method of treating soil by the application, in particular into the seed drill: either of a granular formulation containing the plant health composition of the invention—in combination or as a composition/formulation, or of a mixture of two granular formulations, each containing one of the two active ingredients, with optionally one or more solid or liquid, agriculturally acceptable carriers and/or optionally with one or more agriculturally acceptable surfactants. This method is advantageously employed in seed-beds of cereal, maize, cotton and sunflower. The rates for each active ingredient may be in the range of 10 to 1000 g/ha, as for example 50 to 500 g/ha or 50 to 200 g/ha.

The seed treatment application is carried out by spraying or dusting the seeds before sowing of the plants and before emergence of the plants.

In the treatment of seeds the corresponding formulations are applied by treating the seeds with an effective amount of component (I) and optionally at least one component (II). Herein, the application rates of the composition of the invention are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher. In seed treatment applications in which component (I) is derived from a whole broth of the *Bacillus subtilis* strain or its mutants the number of colony forming units (CFU) applied is important and is generally from $1\times10^8$ through $1\times10^{12}$ per acre, preferably from $1\times10^9$ through $1\times10^{13}$ per acre or, in particular from $1\times10^{10}$ through $1\times10^{12}$ per acre.

The following examples shall illustrate the invention without limiting it. All plants in the experiments listed below, could grow under essentially non-existent pathogen pressure.

EXAMPLE 1: TOMATO

*Bacillus subtilis* QST 713 was used to treat tomato seeds via a quasi-soil drench in the greenhouse. Specifically, tomato seeds were planted in steam-sterilized trays containing sterile media and grown in the greenhouse using standard techniques. Serenade® ASO, which is a liquid formulation of *Bacillus subtilis* QST 713 containing $1\times10^9$ CFU (Colony Forming Units)/g was applied to media at rates of 4 oz, 8 oz, and 16 oz per acre once, at the time of planting. The Serenade® ASO product was applied as a spray application and not as a true drench, as the spray application did not provide enough water to cause germination. Other seeds not treated with the Serenade® ASO product were used as negative controls.

At the time of transplanting to the field, plants grown in media treated with Serenade® ASO showed a higher vigor than those in the untreated control group based on grower observations of plant height, size of root mass as well as color and spindliness of leaves. In addition, a higher percentage of plants treated with the Serenade® ASO product were able to be used in the field than those in the untreated control group (table 1a).

TABLE 1a

| Treatment | Plants that were able to be used in the field (%) |
|---|---|
| Control | 80.3 |
| Serenade ® ASO 4 oz | 83.0 |
| Serenade ® ASO 8 oz | 88.3 |
| Serenade ® ASO 16 oz | 87.7 |

As can be seen in table 1a, Serenade ASO has a positive effect on plant health by increasing the plant's vigor resulting in an increased number of plants that could be used for planting in the field.

Useable transplants treated with Serenade ASO and controls were subsequently planted in the field and grown under the same standard conditions (with all receiving the same watering, pesticide applications, and the like) until harvest. Due to the pesticide application, the plants could grow under essentially non-existent pathogen pressure. At harvest, plants treated with Serenade ASO at the time of planting in the greenhouse yielded more total weight of tomatoes and more marketable tomatoes than the untreated control (table 1b).

TABLE 1b

| Treatment | Yield (Total weight of tomatoes in 12 plots, each containing 2 plants) | Marketable tomatoes (%) |
|---|---|---|
| Control | 359 | 46 |
| Serenade ® ASO 4 oz/ac | 366 | 78 |
| Serenade ® ASO 8 oz/ac | 397 | 71 |
| Serenade ® ASO 16 oz/ac | 368 | 77 |

As can be seen in table 1 b, Serenade® ASO has also a positive effect on plant health by increasing the plant's yield (total weight of tomatoes). In addition, the treatment with Serenade® ASO results in increased vigor of the plants and cosequently in more marketable tomatoes compared to the untreated control plants.

EXAMPLE 2: PEPPER

*Bacillus subtilis* QST 713 was used to treat pepper seeds via a quasi-soil drench in the greenhouse. Specifically, pepper seeds were planted in steam-sterilized trays containing sterile media and grown in the greenhouse using standard techniques. Serenade® ASO, which is a liquid formulation of *Bacillus subtilis* QST 713 containing $1\times109$ CFU/g, was applied to media at rates of 4 oz, 8 oz, and 16 oz per acre once, at the time of planting. The Serenade® ASO product was applied as a spray application and not as a true drench, as the spray application did not provide enough water to cause germination. Other seeds not treated with the Serenade® ASO product were used as negative controls.

At the time of transplanting to the field, plants grown in media treated with Serenade® ASO showed a higher vigor than those in the untreated control group based on grower observations of plant height, size of root mass as well as color and spindliness of leaves. In addition, a higher percentage of plants treated with the Serenade® ASO product were able to be used in the field compared to those in the untreated control group (table 2).

TABLE 2

| Treatment | Vigor (0 = no vigor; 10 = optimal vigor) | Plants that were able to be used in the field (%) |
|---|---|---|
| Control | 3.7 | 95.3 |
| Serenade ® ASO 4 oz/ac | 4.0 | 96.0 |
| Serenade ® ASO 8 oz/ac | 5.3 | 97.0 |
| Serenade ® ASO 16 oz/ac | 6.7 | 97.0 |

As can be seen in table 2, Serenade® ASO has a positive effect on plant health by increasing the plant's vigor. In addition, the treatment with Serenade® ASO results in more plants that were able to be used in the field compared to the untreated control plants which in turn will result in an increased overall yield.

EXAMPLE 3: BROCCOLI

*Bacillus subtilis* QST 713 was used to treat broccoli seeds via a quasi-soil drench in the greenhouse. Specifically, broccoli seeds were planted in steam-sterilized trays containing sterile vermiculite and grown in the greenhouse using standard techniques. Serenade® ASO, which is a liquid formulation of *Bacillus subtilis* QST 713 containing $1\times10^9$ CFU/g, was applied to media at rates of 4 oz, 8 oz, and 16 oz per acre once, at the time of planting. The Serenade®

ASO product was applied as a spray application and not as a true drench, as the spray application did not provide enough water to cause germination. Other seeds not treated with the Serenade® ASO product were used as negative controls.

At the time of transplanting to the field, plants grown in media treated with Serenade® ASO showed a higher vigor than those in the untreated control group based on grower observations of plant height, size of root mass, as well as color and spindliness of leaves. In addition, a higher percentage of plants treated with the Serenade® ASO product were able to be used in the field compared to those in the untreated control group (table 3).

As can be seen in table 3, Serenade® ASO has a positive effect on plant health by increasing the plant's vigor. In addition, the treatment with Serenade® ASO results in more plants that were able to be used in the field compared to the untreated control plants which in turn will result in an increased overall yield.

TABLE 3

| Treatment | Vigor (0 = no vigor; 10 = optimal vigor) | Plants that were able to be used in the field (%) |
| --- | --- | --- |
| Control | 4.7 | 91.7 |
| Serenade ® ASO 4 oz/ac | 6.0 | 92.0 |
| Serenade ® ASO 8 oz/ac | 7.3 | 93.0 |
| Serenade ® ASO 16 oz/ac | 5.3 | 93.0 |

EXAMPLE 4: WHEAT

Wheat seed was treated with *Bacillus subtilis* QST 713 by applying to the seeds a slurry of the Serenade® ASO product at a rate of 4 oz, 8 oz, 12 oz or 16 oz per 100 lb seed. The slurry was prepared by mixing Serenade® ASO with water. Seeds remained in the slurry for various periods of time, ranging from overnight to two weeks. Fields were seeded at a rate of 80-100 lb per acre. Seeds were applied to fields in which disease pressure was essentially non-existent. Consequently, growers would typically not engage in seed treatment for disease control.

TABLE 4

| Treatment | Yield (bushels/acre) |
| --- | --- |
| Control | 49.9 |
| Difenoconazole + mefenoxam | 65.7 |
| Serenade ® ASO 4 oz + difenoconazole + mefenoxam | 79.5 |
| Serenade ® ASO 4 oz/100 lb seed | 100.4 |
| Serenade ® ASO 8 oz/100 lb seed | 90.8 |
| Serenade ® ASO 12 oz/100 lb seed | 49.3 |
| Serenade ® ASO 16 oz/100 lb seed | 34.6 |

As can be seen in table 4, Serenade® ASO has a very positive effect on plant health by increasing the yield when applied below 10 oz/100 lb seed. When applied at higher amounts with this particular formulation, the yield may remain unaffected or may even decline. However, it is unknown whether this decline is due to a formulation inert in this particular formulation or due to the rate of active ingredient. One of ordinary skill in the art would be able to determine the optimal rate of application of component (I) with routine experimentation.

EXAMPLE 5: WHEAT

The Serenade® ASO product, which contains 1×109 CFU/g *Bacillus subtilis* QST 713 was applied in furrow at the time of wheat seed planting along with the following starter fertilizer: 10-34-0 (10% nitrogen, 34% phosphate and 0% potassium) and/or Power Up (6% nitrogen, 18% phosphate and 6% potassium) at the rates/per acre shown below. Disease pressure was essentially non-existent, such that disease rates were not reported for this trial. This was a situation in which a grower would not typically apply the Serenade® ASO product, as the cost would not be justified from a disease control perspective.

TABLE 5

| Treatment | Yield (bushels/acre) |
| --- | --- |
| Control | 21.7 |
| 3 gallons per acre (gpa) of 10-34-0 | 25.9 |
| 2 gpa of 10-34-0 + 1 gpa Power Up | 28.3 |
| 2 gpa of 10-34-0 + 1 gpa Power Up + Serenade ® ASO 8 oz/ac | 31.0 |
| 2 gpa of 10-34-0 + 1 gpa Power Up + Serenade ® ASO 16 oz/ac | 30.1 |

As can be seen in table 5, the application of Serenade® ASO with the fertilizers resulted in an increased yield. In addition, in the case of in-furrow application of Serenade® ASO, wheat heads displayed advanced maturity compared to the untreated control plants in which only 75% of the wheat heads had formed at the same time point.

EXAMPLE 6: LETTUCE

The active compounds were used applying commercially available formulations and diluted according to the concentrations/dose rates as stated in table 6. Commercially available lettuce seedlings ("Eichblatt") were used for the described greenhouse trial. 4 replications (pots with 1 plant each) were used per treatment. Plants were grown in commercially available substrate (Floradur A) at approx. 20° C. in the greenhouse. Drench applications using a volume of 25 ml of product solution or water (Control) were made on 16 consecutive days. On the last day, fresh weight was determined using all plant parts above ground.

TABLE 6

| Treatment | Yield Fresh weight (g) |
| --- | --- |
| Control | 51.7 |
| Serenade ® MAX 312 ppm | 59.5 |
| Serenade ® MAX 625 ppm | 62.4 |
| Serenade ® MAX 1250 ppm | 74.1 |
| Serenade ® MAX 2500 ppm | 68.9 |

As can be seen from table 6, Serenade® MAX strongly increases the fresh weight of lettuce plants which is an essential parameter for vegetables.

EXAMPLE 7: SOYBEANS

Soybeans were planted in December 2008 at the BASF experimental station in Campinas, San Antonio de Posse, Sao Paulo, Brazil. The variety Emprapa 48 was planted at a seeding rate of 300,000 plants per ha. Row spacing was 45 cm. Two trials were setup as a randomized bloc design with 6 replications. Plot size was 20 m².

*Bacillus subtilis* QST 713 was applied by foliar application to the vegetative parts of the soybean plants at developmental stage 23/29 (BBCH) followed by the foliar application of either *Bacillus subtilis* QST 713 alone or in tank mix with pyraclostrobin (applied as COMET® at the beginning of flowering at the developmental stages 60/63 (BBCH). The active ingredients were applied using the commercial formulations Serenade® (10%, WP with 5×109 cfu/g) and Comet® (250 g/L, EC). The formulations were used in the dose rates given in table 7. Total spray volume for foliar applications was 150 l/ha. Serenade® was applied with 3 kg product per ha and Comet® applied with a product rate of 0.4 l/ha. At maturity the crop was harvested and grain yield was measured in t/ha. Green leaf area was assessed 31 days after the last treatment (table 7) by estimating the green leaf area in 10 randomly chosen plants per plot.

The efficacy (E) was calculated as % increase of green leaf area in the treatments compared to the untreated control according to the following formula:

$$E = a/b - 1 \cdot 100$$

E efficacy a corresponds to the green leaf area (%) of the treated plants and b corresponds to the green leaf area (%) of the untreated (control) plants An efficacy (E) of 0 means the green leaf area of the treated plants corresponds to that of the untreated control plants; an efficacy of 100 means the treated plants showed an increase in the green leaf area of 100%.

TABLE 7

| Treatment | PR | FC | FT | AT | GLA (%) | GLAE (%) | Grain Yield (t/ha) |
|---|---|---|---|---|---|---|---|
| Untreated |  |  |  |  | 7.5 |  | 1.97 |
| Serenade ® | 3.0 kg/ha | 10% | WP | 23/29 | 12.5 | 66.6 | 2.30 |
|  | 3.0 kg/ha | 10% | WP | 60/63 |  |  |  |
| Serenade ® | 3.0 kg/ha | 10% | WP | 23/29 | 20.0 | 166.6 | 3.08 |
|  | 3.0 kg/ha | 10% | WP | 60/63 |  |  |  |
| Pyraclostrobin | 0.3 l/ha | 250 g/l | EC | 60/63 |  |  |  |

PR = Product rate;
FC = Formulation concentration;
FT = Formulation type;
AT = Application time (BBCH);
GLA = Green Leaf Area; Green Leaf Area (Efficacy)

As can be seen in table 7, Serenade® clearly increases the green leaf area duration (maintanance of green leaves) and the grain yield in soybeans compared to the untreated control. In addition, the results shown in table 7 demonstrate that the efficacy of the combination of Serenade® and pyraclostrobin is even higher than for Serenade alone. An increase of the green leaf area is a visible sign of the enhanced plant vigor. Based on a prolonged maintanance of green leaves which in turn results in a prolonged photosynethic activity of the leaves as well as an overall srengthening of the plant, the plant is able to produce a higher yield.

EXAMPLE 8: SOYBEANS

Soybeans were planted in 2009 at 9 locations across the soybean growing area of Midwest of the USA (IN, IL, IA, MO, NE, and SD). Planting dates ranched from May 7th at York, Neb., to June 22nd at Clarence, Mo. *Bacillus subtilis* QST 713 was applied to the vegetative parts of the soybean plants at developmental stage 23/29 (BBCH). The *B. subtilis* QST 713 was applied using the commercial formulation Serenade Max® (14.3%, WP with 7.3×109 cfu/g). Serenade Max® was used in the dose rates given in Table 8. Total spray volume for foliar application ranched from 140 to 200 l/ha. Serenade Max® was applied at 3 kg product per ha. At maturity the crop was harvested and grain yield was measured as t/ha (table 8). Green leaf area was assessed 36 to 66 days after the last treatment on seven of the trial locations (table 8) by estimating the green leaf area in 10 randomly chosen plants per plot. The efficacy was calculated as indicated above.

TABLE 8

| Treatment | PR | FC | FT | AT | GLA (%) | GLAE (%) | Grain Yield (t/ha) |
|---|---|---|---|---|---|---|---|
| Untreated |  |  |  |  | 64.36 |  | 34.87 |
| Serenade ® MAX | 3.0 kg/ha | 14.3% | WP | 23/29 | 67.04 | 4.2 | 36.42 |

PR = Product rate;
FC = Formulation concentration;
FT = Formulation type;
AT = Application time (BBCH);
GLA = Green Leaf Area; Green Leaf Area (Efficacy)

As can be seen in table 8, Serenade Max® increases the green leaf area duration and therefore improve photosynthetic activity of soybeans. In addition, Serenade Max® strongly increases the grain yield; in this case by 1.55 t/ha in soybeans compared to the untreated control by improving the vigor of the soybean plants.

EXAMPLE 9: WINTER WHEAT

Winter wheat was grown in the 2008/2009 growing season at 4 locations across Germany (Thuringia, Baden-Wuerttemberg, and Rhineland-Palatinate). Seeding of the crop ranged from September 21st to October 26th. The trials were setup in a randomized bloc design with 6 replications. *Bacillus subtilis* QST 713 was applied to the winter wheat plants at beginning of shooting (growth stage 31/32, BBCH). The fungicide spray sequence consisted of an application of epoxiconazole at beginning of shooting followed by an application of epoxiconazole in combination with pyraclostrobin at flag leaf stage (growth stage 37/39). The *B. subtilis* QST 713 was applied using the commercial formulation Serenade Max® (14.3%, WP with 7.3×109 cfu/g). Epoxiconazole was applied alone at beginning of shooting as the commercially available formulation Opus® (125 g/l, SC). The combination of epoxiconazole and pyraclostrobin was applied as a ready to use developmental Opera® formulation (SE) containing 62.5 g/l epoxiconazole and 85 g/l pyraclostrobin. Product rates are given in table 9. Total spray volume for the foliar applications were 300 l/ha. At maturity the crop was harvested and grain yield was measured as t/ha (table 9).

TABLE 9

| Treatment | PR | FC | FT | AT | Grain Yield (t/ha) | Observed yield increase (t/ha) |
|---|---|---|---|---|---|---|
| Untreated | | | | | 6.73 | |
| Epoxiconazole | 0.8 l/ha | 125 g/l | SC | 31/32 | 7.78 | 1.05 |
| Epoxiconazole + Pyraclostrobin | 2.0 l/ha | 147.5 | SE | 37/39 | | |
| Serenade Max ® | 3.0 kg/ha | 14.3% | WP | 31/32 | 6.87 | 0.14 |
| Serenade Max ® | 3.0 kg/ha | 14.3% | WP | 31/32 | 7.93 | 1.20 |
| Epoxiconazole | 0.8 l/ha | 125 g/l | SC | 31/32 | | |
| Epoxiconazole + Pyraclostrobin | 2.0 l/ha | 147.5 | SE | 37/39 | | |

PR = Product rate;
FC = Formulation concentration;
FT = Formulation type;
AT = Application time (BBCH);

As can be seen in table 9, the Serenade Max® treatment increased the yield of the wheat crop by 140 kg/ha. The joint application with an application sequence of Serenade Max® together with the fungicide spray of epoxiconazole and epoxiconazole plus pyraclostrobin was even superior compared to the application of the fungicides (epoxiconazole plus pyraclostrobin) alone (1.2 vs. 1.05 t/ha). These findings demonstrate the improvement of the vigor of the wheat plants by *Bacillus subtilis* QST 713 and the superior effect of the combination of *Bacillus subtilis* QST 713 with fungicides compared to the effect of the solo application of *Bacillus subtilis* QST 713 or an application of a composition comprising as active ingredients only fungicides.

EXAMPLE 10: MAIZE (CORN)

Maize was planted in 2009 at Carlyle, Ill., USA. The variety Burrus 616XLR was planted at a conventional seeding rate and a row spacing of 76 cm. The trial was setup as a randomized bloc design with 6 replications. Plot size was 18 m². Pyraclostrobin was applied at developmental stage 34/37 (BBCH). *Bacillus subtilis* QST 713 (Serenade Max®) was applied to the maize plants at developmental stage 34/37 (BBCH) followed by a second application at developmental stage 55/57 (BBCH). *Bacillus subtilis* QST 713 (Serenade Max®) in combination with pyraclostrobin were applied as a tank mix at the developmental stage 34/37 (BBCH). The active ingredients were applied using commercial formulations Serenade Max® (14.3%, WP with 7.3×109 cfu/g) and Headline® (250 g/L, EC). The formulations were used in the dose rates given in table 10. Total spray volume for foliar applications was 200 l/ha. Serenade Max® was applied with 2.1 kg product per ha and Headline® with a product rate of 0.44 l/ha. At maturity the crop was harvested and grain yield was measured as t/ha (table 10).

The expected yield increase by the combination of the active compounds was estimated using Colby's formula (Colby, S. R., Calculating synergistic and antagonistic responses of herbicide combinations, Weeds, 15, pp. 20-22, 1967) and compared with the observed yield increase.

$$E = x + y - x \cdot y / 100 \qquad \text{Colby's formula:}$$

E expected efficacy, expressed as the numerical difference of the yield in t/ha to the untreated control, when using the mixture of the active compounds A and B at the concentrations a and b x efficacy, expressed as the numerical difference of the yield in t/ha to the untreated control, when using the active ingredient A at the concentration a y efficacy, expressed as the numerical difference of the yield in t/ha to the untreated control, when using the active ingredient B at the concentration b

TABLE 10

| Treatment | PR | FC | FT | AT | Grain Yield (t/ha) | Observed yield increase (t/ha) | Expected yield increase (t/ha) |
|---|---|---|---|---|---|---|---|
| Untreated | | | | | 8.27 | | |
| Pyraclostrobin | 0.44 l/ha | 250 g/l | EC | 34/37 | 8.32 | 0.05 | |
| Serenade Max ® | 3.0 kg/ha 3.0 kg/ha | 14.3% | WP | 34/37 55/57 | 8.42 | 0.15 | |
| Serenade Max ® Pyraclostrobin | 3.0 kg/ha 0.3 l/ha | 14.3% 250 g/l | WP EC | 34/37 | 8.66 | 0.39 | 0.19 |

PR = Product rate;
FC = Formulation concentration;
FT = Formulation type;
AT = Application time (BBCH);

Application of Serenade Max® alone and the combination of Serenade Max® and pyraclostrobin results in a clear yield increase. Compared to the yield increase of the solo application of Serenade Max® or pyraclostrobin solo, the yield increase when the combination of Serenade Max® and pyraclostrobin were applied togehter is even higher than could have been expected according to Colby's formula. This yield increase, which is about double as high as expected, clearly demonstrates the synergistic effect of the compositions according to the invention on the plant's vigor and the plant's yield.

EXAMPLE 11: WINTER WHEAT

Winter wheat was grown in the 2008/2009 growing season at Cagnicourt in France. The variety Premio was sown November 1st at a seeding rate of 125 kg/ha. The trial was setup in a randomized bloc design with 6 replications and a plot size of 22.5 m². *Bacillus subtilis* QST 713 was applied to the winter wheat plants at beginning of shooting (growth stage 31/32, BBCH). The fungicide spray sequence consisted of an application of epoxiconazole at beginning of shooting followed by an application of epoxiconazole in combination with pyraclostrobin at flag leaf stage (growth stage 37/39). The *B. subtilis* QST 713 was applied using the commercial formulation Serenade Max® (14.3%, WP with 7.3×109 cfu/g). Epoxiconazole was applied alone at beginning of shooting as the commercially available formulation Opus® (125 g/l, SC). The combination of epoxiconazole and pyraclostrobin was applied as a ready to use developmental Opera formulation (SE) containing 62.5 g/l epoxiconazole and 85 g/l pyraclostrobin. Product rates are given in table 11. Total spray volume for the foliar applications were 300 l/ha. At end of heading and beginning of flowering, respectively, the number ears per m² was counted (table 11). The expected increase in number of ears per m² by the combination of the active compounds was estimated using Colby's formula (Colby, S. R., Calculating synergistic and antagonistic responses of herbicide combinations, Weeds, 15, pp. 20-22, 1967) and compared with the observed increase as described above.

TABLE 11

| Treatment | PR | FC | FT | AT | No. of Ears/m² | Observed increase | Expected increase |
|---|---|---|---|---|---|---|---|
| Untreated | | | | | 375 | | |
| Epoxiconazole | 0.8 l/ha | 125 g/l | SC | 31/32 | 394 | 19 | |
| Epoxiconazole + Pyraclostrobin | 2.0 l/ha | 147.5 | SE | 37/39 | | | |
| Serenade Max ® | 3.0 kg/ha | 14.3% | WP | 31/32 | 385 | 10 | |
| Serenade Max ® | 3.0 kg/ha | 14.3% | WP | 31/32 | 406 | 31 | 27 |
| Epoxiconazole | 0.8 l/ha | 125 g/l | SC | 31/32 | | | |
| Epoxiconazole + Pyraclostrobin | 2.0 l/ha | 147.5 | SE | 37/39 | | | |

PR = Product rate;
FC = Formulation concentration;
FT = Formulation type;
AT = Application time (BBCH);

In this example, again, Serenade Max® improved the health of the wheat plants leading to increased number of ears per m². An increased number of ears per m² was also observed from the fungicide spray sequence. The increase observed from the combined application of Serenade Max® and the fungicides was higher than expected according to Colby's formula, as is shown in table 11. This result clearly illustrates the synergistic effect of the combination of *Bacillus subtilis* QST 713 with azoles and strobilurins on the vigor and yield of the wheat plants when applied together in a tank mix or a spray sequence.

EXAMPLE 12: PEAS

The active compounds were used applying commercially available formulations and diluted according to the concentrations/dose rates as stated in the respective data tables.

Seed treatment was done to seeds of peas using the Hege Seed Treatment equipment in a sequential approach. Pyraclostrobin was applied with a volume of 850 ml slurry per 100 kg seeds. Afterwards the stated amount of Serenade® MAX was dissolved in a total volume of 8.3 L water (amount for 100 kg seeds) and applied sequentially in ten steps with drying of the seeds inbetween. The compounds were used as commercial finished formulations and diluted with water to the stated concentration of the active compound.

Seeds of peas were sown in soil (10 seeds/pot, 10 replications/treatment) and incubated in the greenhouse at 20° C. for 12 days. Plants were harvested and pooled per treatment and the plant fresh weight was determined.

The expected plant fresh weights of active compound mixtures were determined using Colby's formula as defined above [R. S. Colby, "Calculating synergistic and antagonistic responses of herbicide combinations", Weeds 15, 20-22 (1967)] and compared with the observed plant fresh weights.

As can be seen in table 12, the measured fresh weight when Serenade Max® is applied strongly increases compared to the untreated control plants. In case a mixture according to the present invention is applied such as the combination of Serenade Max® and pyraclostrobin, the fresh weight as an indicator for the plant's vigor and yield is increased even synergistically.

TABLE 12

| Treatment | Dose rate (g/100 kg seed) | Fresh weight (g) | Calculated efficacy according to Colby (%) |
|---|---|---|---|
| Untreated | | 55 | |
| Pyraclostrobin (200 g/L, FS) | 5 | 47 | |
| Serenade Max ® (14.3% *B. subtilis*, WP) | 173 | 64 | |
| Pyraclostrobin + Serenade Max ® | 5 173 | 92 | 81 |

The invention claimed is:

1. A method for increasing the vigor and/or crop yield of agricultural plants,
   wherein the plants, the plant propagules, the seed of the plants and/or the locus where the plants are growing or are intended to grow are treated with an effective amount of a composition comprising the *Bacillus subtilis* strain with NRRL Accession No. B-21661, a mutant of this strain having all the identifying characteristics of the strain, or a cell-free extract thereof; and
   wherein pathogen pressure is non-existent.

2. The method as claimed in claim 1, wherein the increased yield is characterized by increased plant weight, increased plant height, increased biomass, higher grain yield, more tillers, larger leaves, increased shoot growth, increased protein content, increased oil content, increased starch content, and/or increased pigment content.

3. The method as claimed in claim 1, wherein the plants, the plant propagules, the seed of the plants and/or the locus where the plants are growing or are intended to grow are treated with an effective amount of a composition comprising the *Bacillus subtilis* strain with NRRL Accession No. B-21661.

4. The method as claimed in claim 1, wherein treatment with the *Bacillus subtilis* strain with NRRL Accession No. B-21661, mutant of this strain having all the identifying characteristics of the strain or cell-free extract thereof results in an increase in vigor and/or crop yield in the agricultural plants;
  wherein the yield of a product of the plants is increased by at least 5% over the yield of the same product of the plants without application of the composition.

5. The method as claimed in claim 1, wherein the composition comprising the *Bacillus subtilis* strain with NRRL Accession No. B-21661, mutant of this strain having all the identifying characteristics of the strain or cell-free extract thereof increases the vigor and/or crop yield of agricultural plants independently of the pesticidal action of the composition.

6. The method as claimed in claim 1, wherein the seed is treated.

7. The method as claimed in claim 1, wherein the application is carried out as in-furrow and/or foliar treatment.

8. The method as claimed in claim 1, wherein a repeated application is carried out.

9. The method as claimed in claim 1, wherein the *Bacillus subtilis* strain with NRRL Accession No. B-21661, mutant of this strain having all the identifying characteristics of the strain or cell-free extract thereof is applied during the Pre-harvest interval.

10. The method as claimed in claim 1, wherein the agricultural plant is selected from soybean, corn, wheat, triticale, barley, oat, rye, rape, millet, rice, sunflower, cotton, sugar beet, pome fruit, stone fruit, citrus, banana, strawberry, blueberry, almond, grape, mango, papaya, peanut, potato, tomato, pepper, cucurbit, cucumber, melon, watermelon, garlic, onion, broccoli, carrot, cabbage, bean, dry bean, canola, pea, lentil, alfalfa, trefoil, clover, flax, elephant grass, grass, lettuce, sugarcane, tea, tobacco and coffee; each in its natural or genetically modified form.

11. The method as claimed in claim 4, wherein the yield of the product of the plants is increased by at least 10% over the yield of the same product of the plants without application of the composition.

12. The method as claimed in claim 1, wherein a commercially available formulation of the *Bacillus subtilis* strain is used.

13. The method as claimed in claim 2, wherein the increased yield is characterized by higher grain yield.

14. The method as claimed in claim 2, wherein the increased yield is characterized by increased plant height.

15. The method as claimed in claim 2, wherein the increased yield is characterized by increased plant weight.

16. The method as claimed in claim 2, wherein the increased yield is characterized by increased plant biomass.

* * * * *